United States Patent [19]

Nolan et al.

[11] Patent Number: 5,480,406
[45] Date of Patent: Jan. 2, 1996

[54] METHOD OF EMPLOYING SURGICAL SUTURING APPARATUS TO TIE KNOTS

[75] Inventors: Paul Nolan, Wilton; H. Jonathan Tovey, Milford; Corbett W. Stone, Newtown, all of Conn.; Gregory S. Gardner, Owings Mills, Md.

[73] Assignee: United States Surgical Corporation, Norwalk, Conn.

[21] Appl. No.: 319,837

[22] Filed: Oct. 7, 1994

[51] Int. Cl.⁶ .................................................. A61B 17/64
[52] U.S. Cl. ...................... 606/139; 606/144; 606/147; 289/1.2; 289/1.5
[58] Field of Search ............................ 606/139, 142–148; 289/1.2, 1.5, 17

[56] References Cited

U.S. PATENT DOCUMENTS

| | | | |
|---|---|---|---|
| 4,923,461 | 5/1990 | Caspari et al. | 606/146 |
| 4,935,027 | 6/1990 | Yoon | 606/146 |
| 5,037,433 | 8/1991 | Wilk et al. | 606/144 |
| 5,181,919 | 1/1993 | Bergman et al. | 606/144 |
| 5,389,103 | 2/1995 | Melzer et al. | 606/139 |

FOREIGN PATENT DOCUMENTS

| | | |
|---|---|---|
| 0647431 | 10/1994 | European Pat. Off. . |
| 2260704 | 9/1991 | United Kingdom . |

OTHER PUBLICATIONS

Endostitch * Suturing Instrument Intrcorporeal Knot Tying Manual, United States Surgical Corporation Copyright 1994.

*Primary Examiner*—Gary Jackson

[57] ABSTRACT

The disclosure contemplates a method for using an endoscopic suturing apparatus to conveniently place various knots in suture such as a square knot, a modified fisherman's knot, a securing knot, an alternative square knot and a surgeon's knot. The knots are formed variously by placing the suture between the jaws or around one jaw and passing the needle from one jaw to the other to be able to draw the suture through loops formed in the suture.

16 Claims, 12 Drawing Sheets

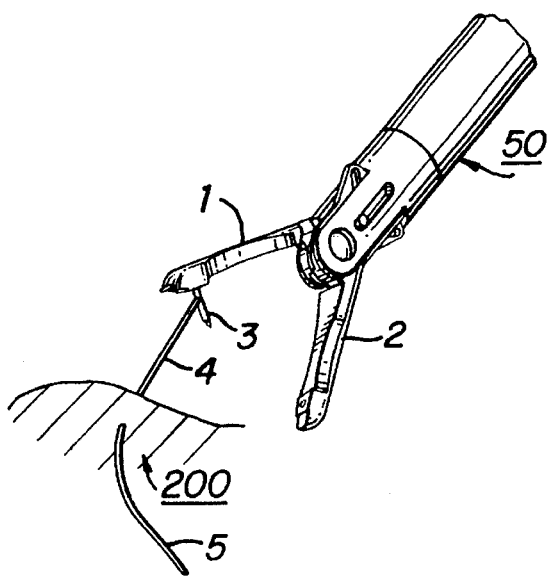
FIG_1
FIG_2
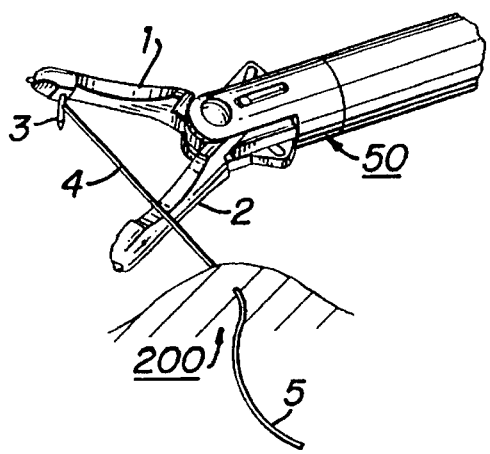
FIG_3
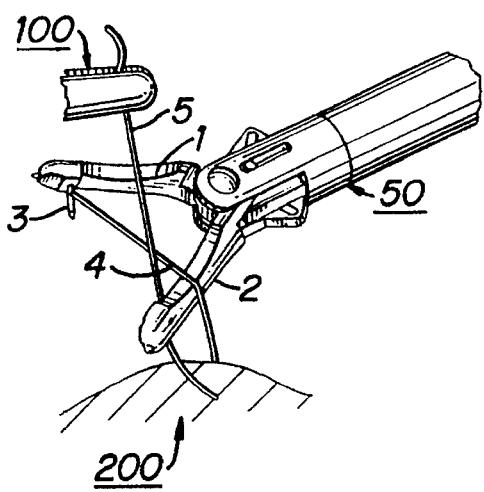
FIG_4
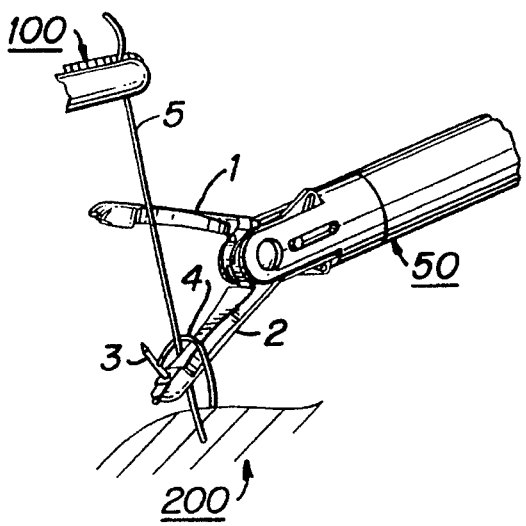

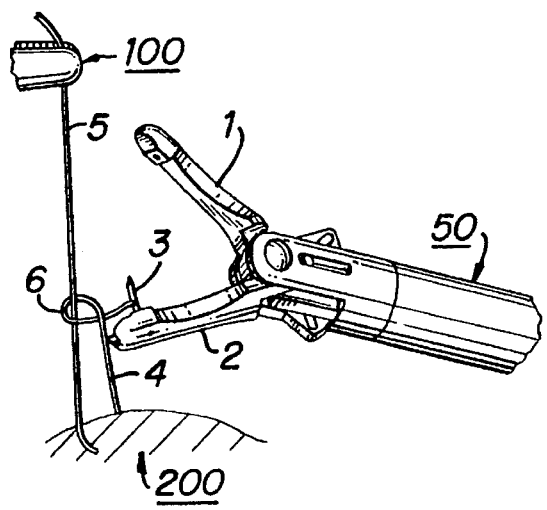
FIG._5
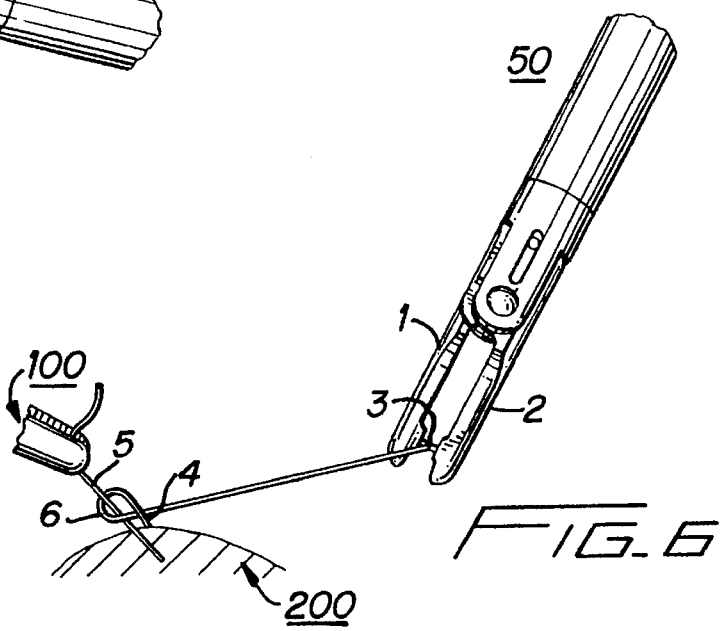
FIG._6
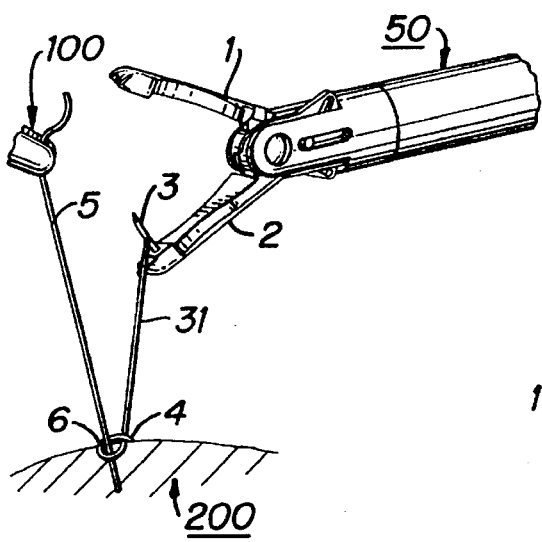
FIG._7
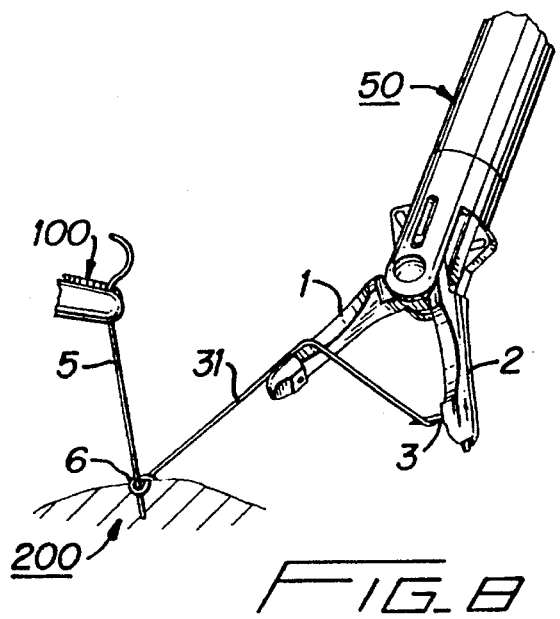
FIG._8

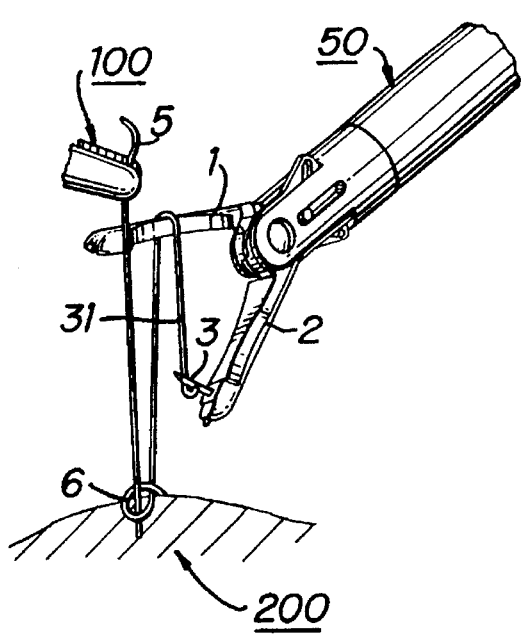
FIG_9
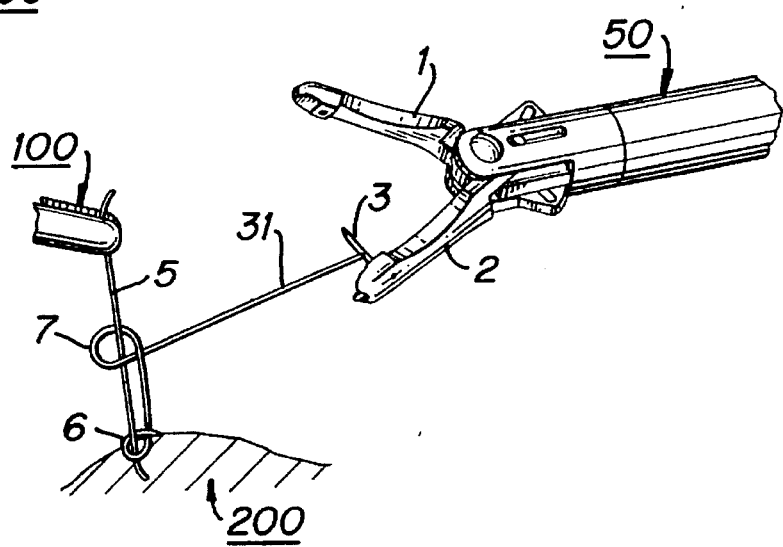
FIG_10
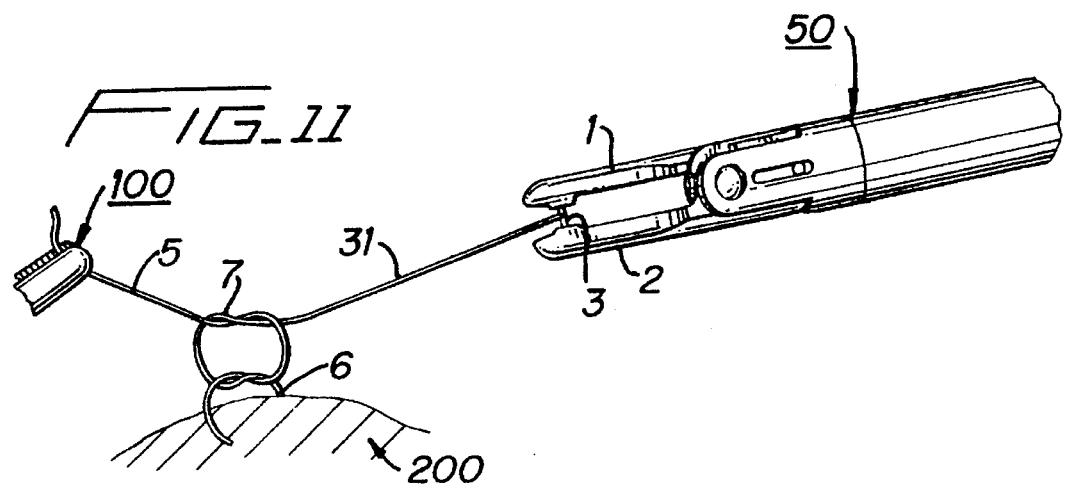
FIG_11

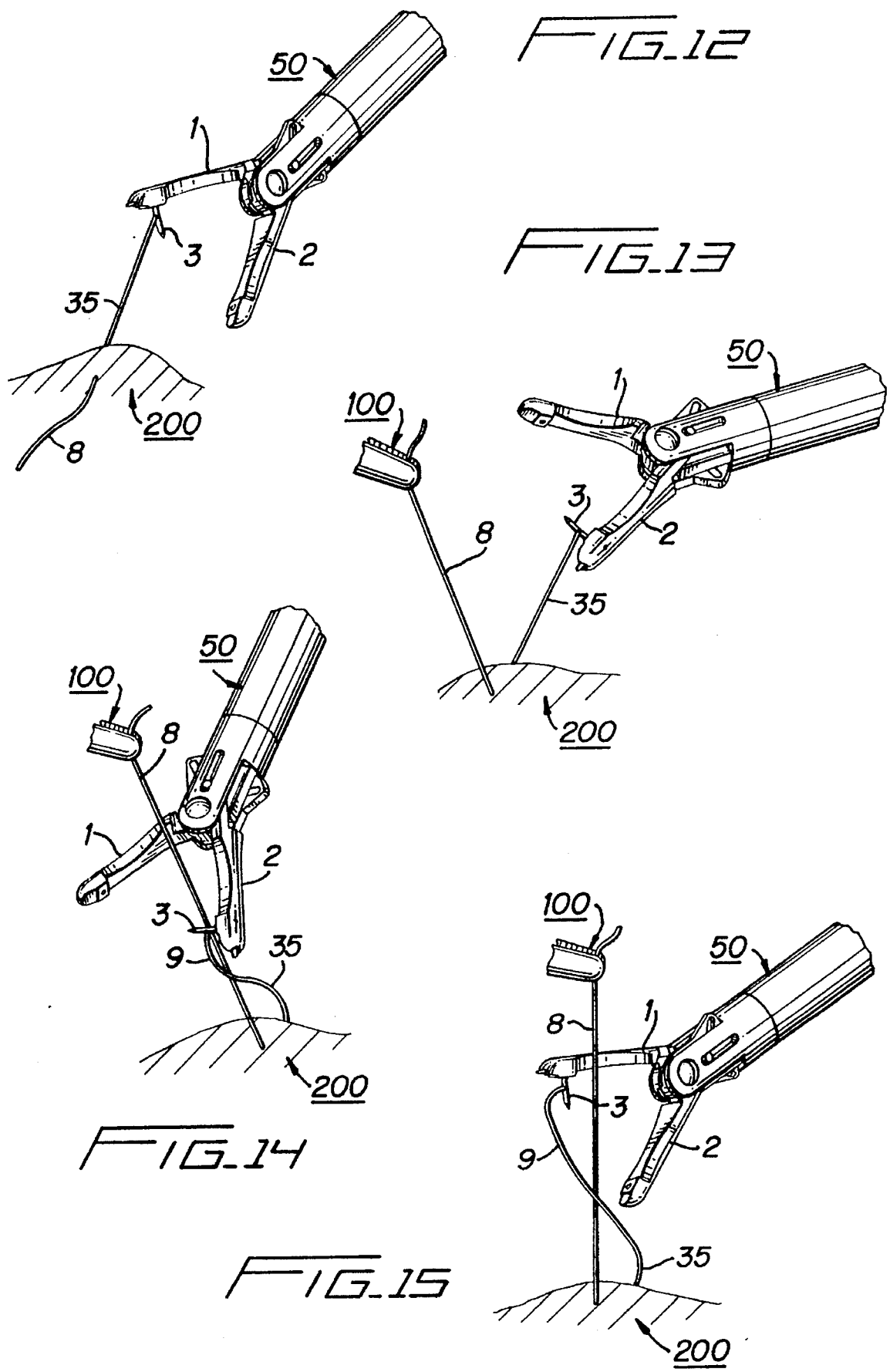

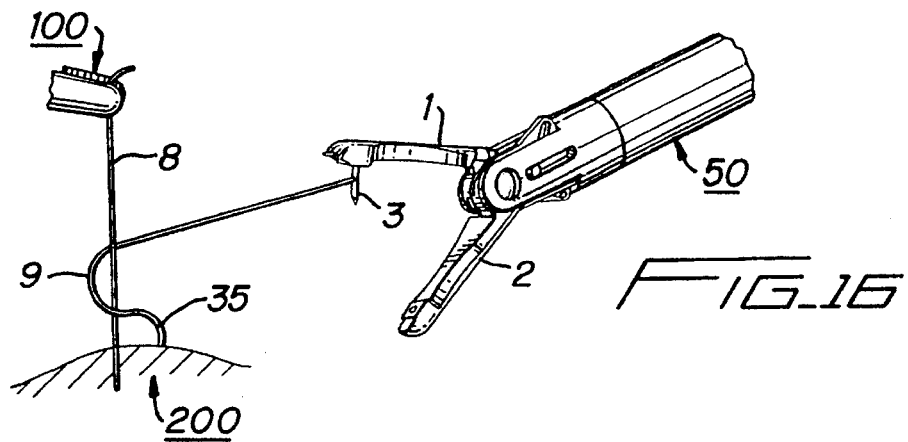
FIG_16
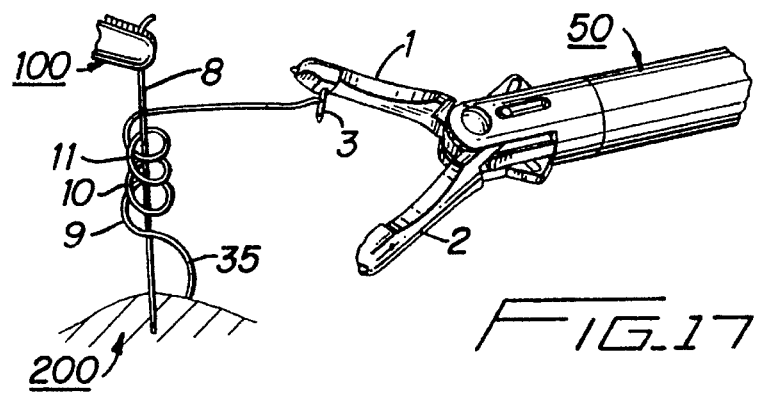
FIG_17
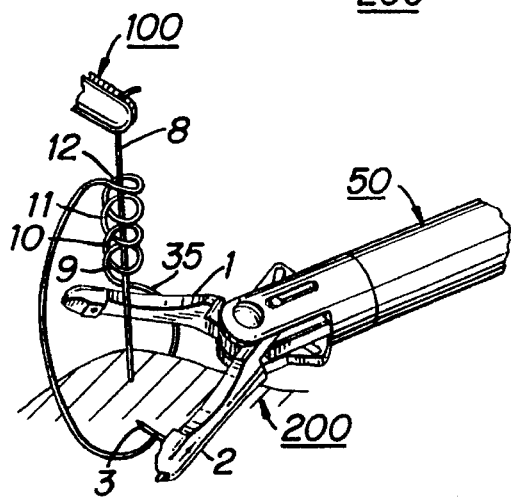
FIG_18
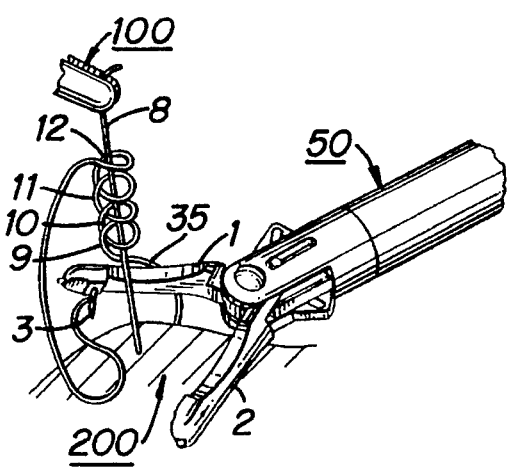
FIG_19

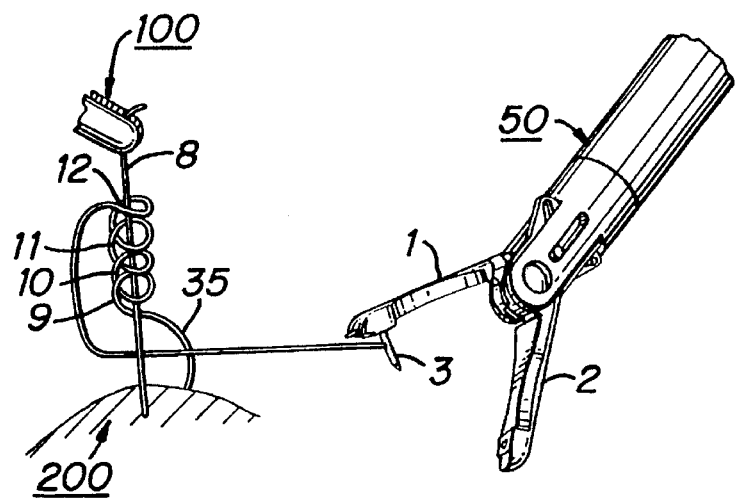
FIG_20
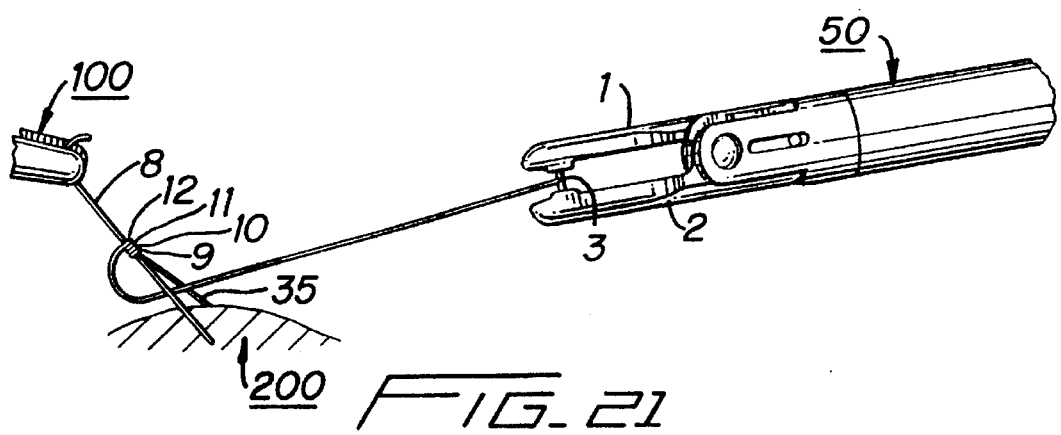
FIG_21
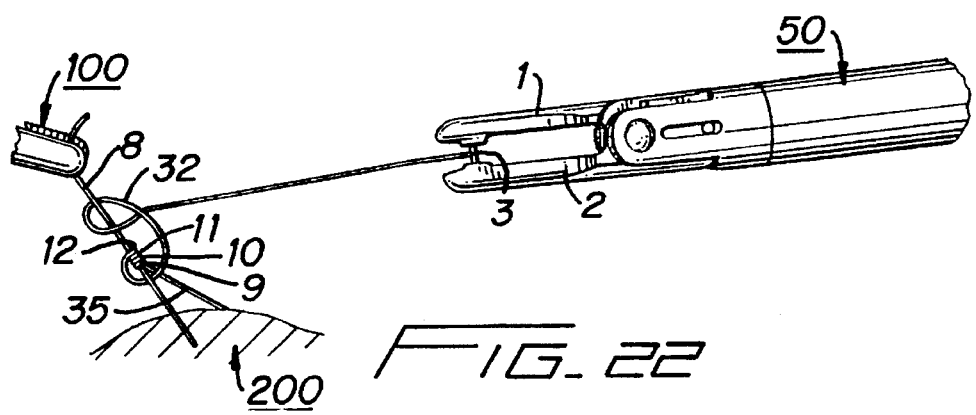
FIG_22

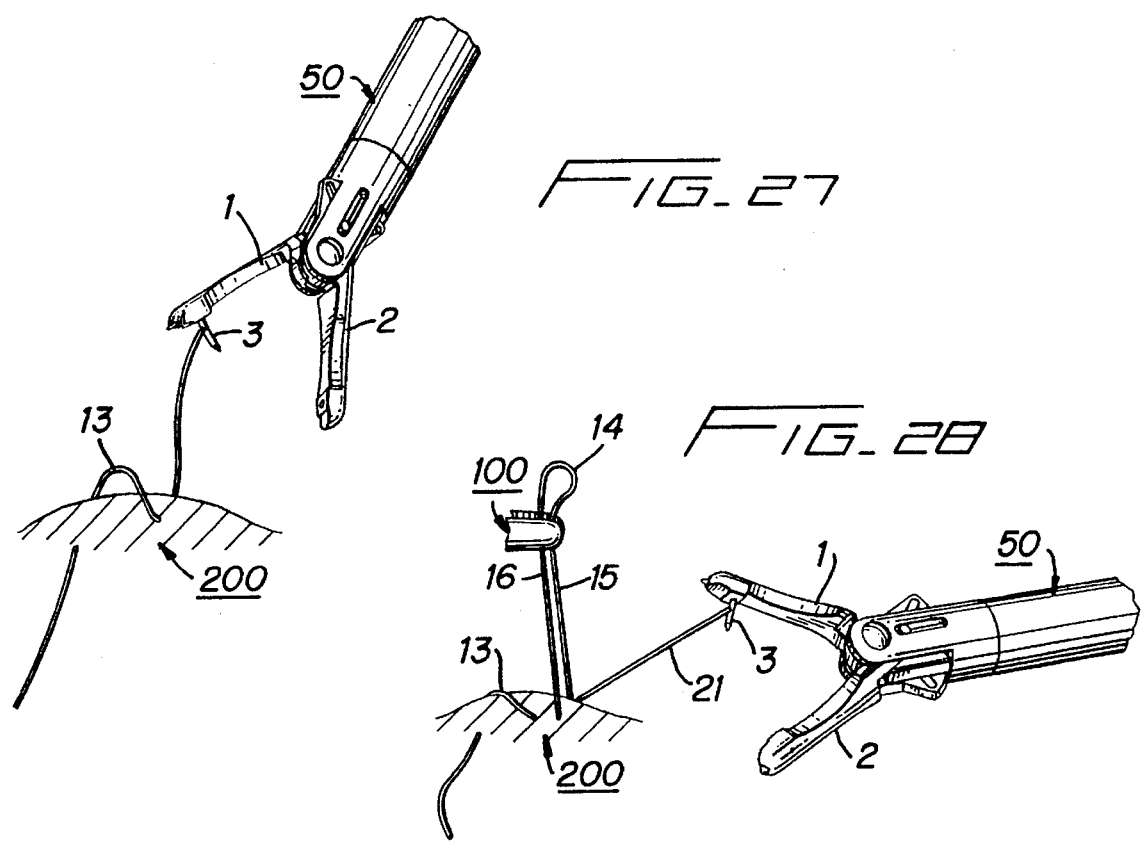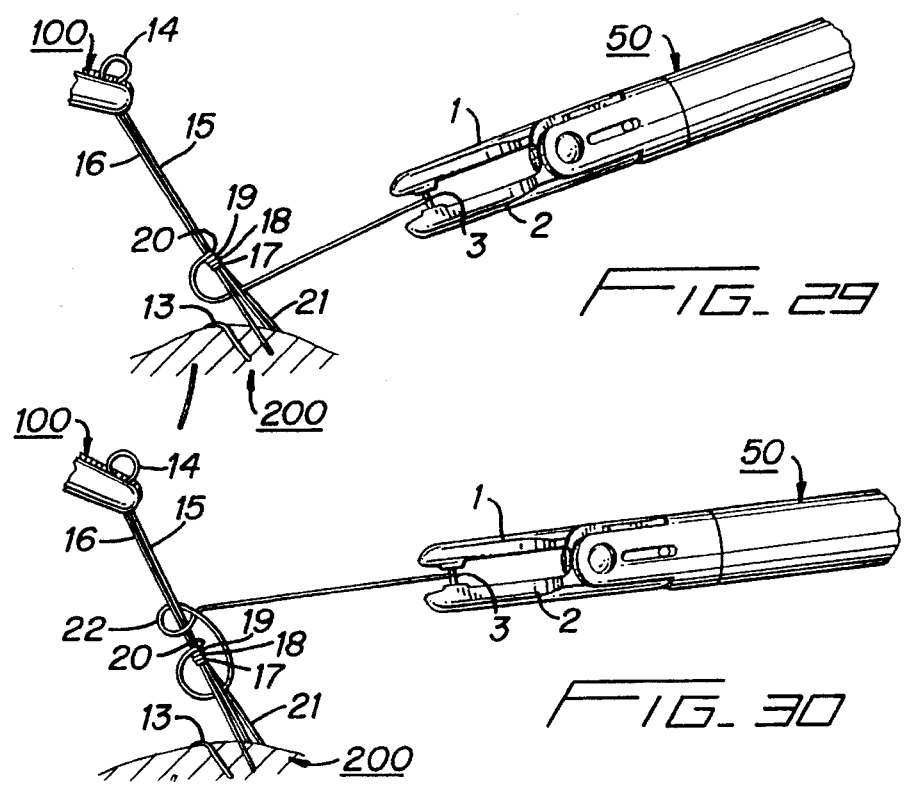

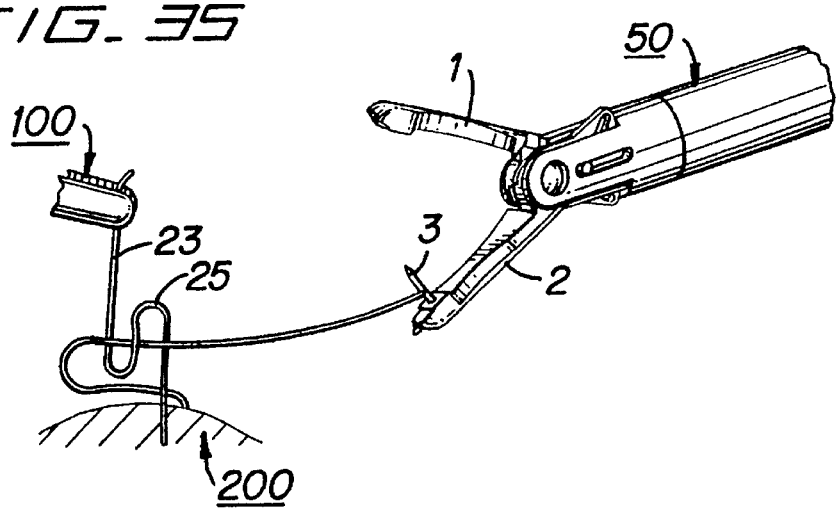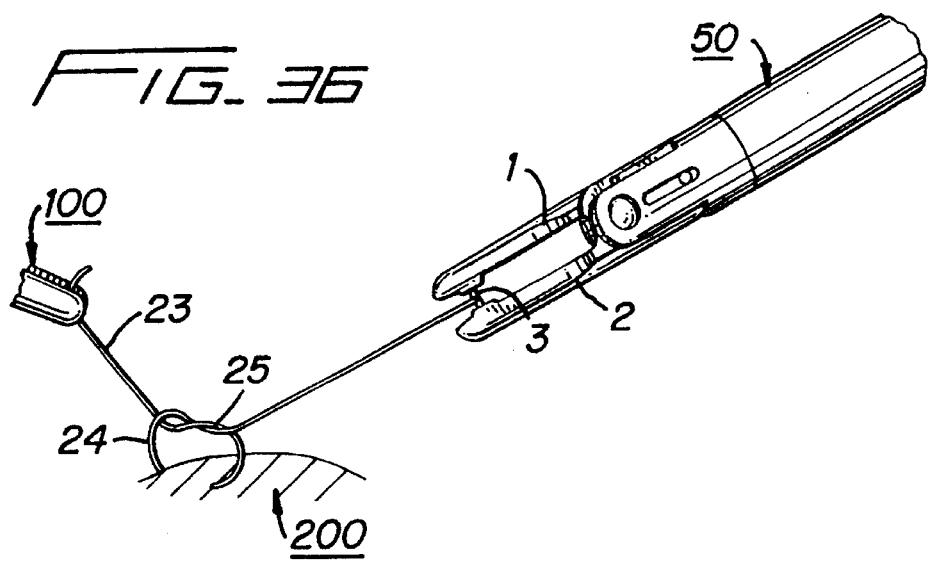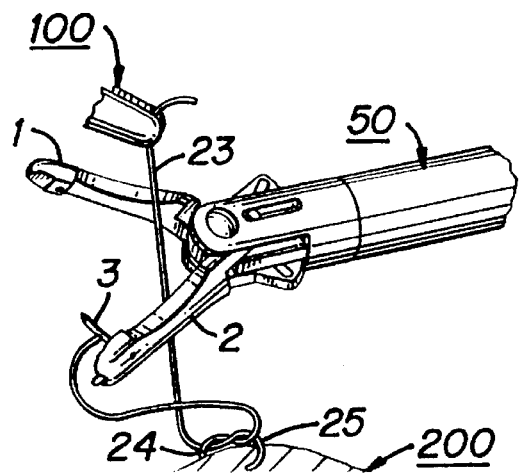

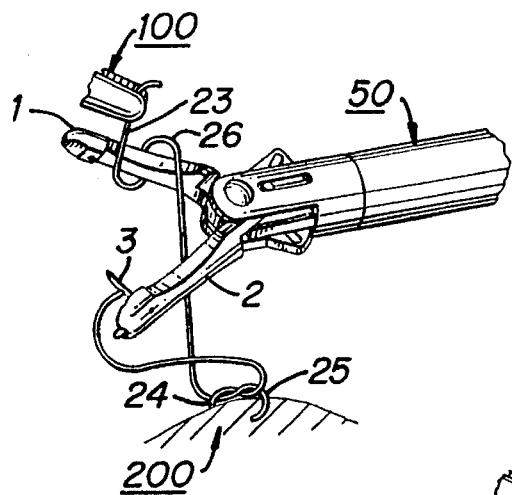
FIG_38
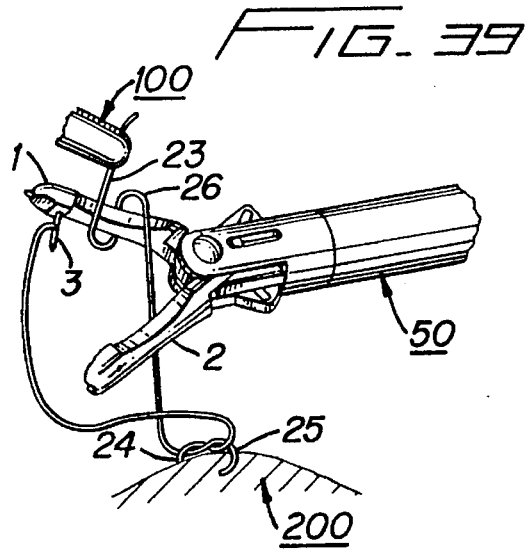
FIG_39
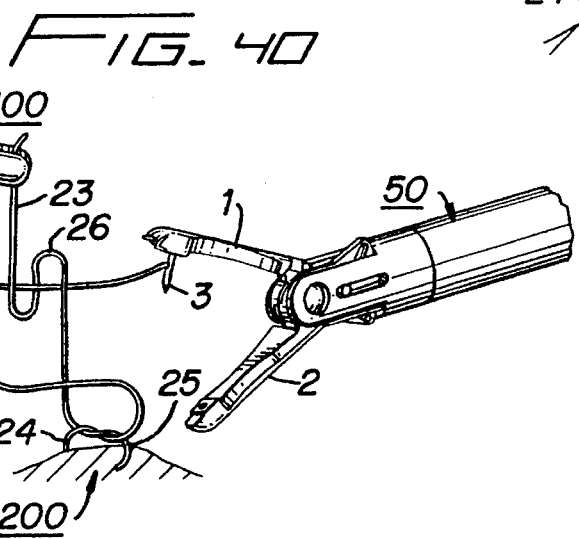
FIG_40
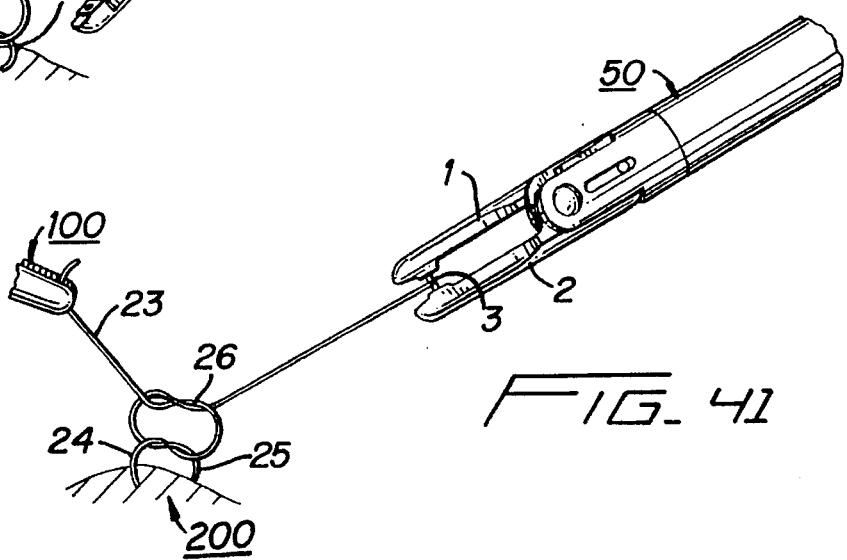
FIG_41

METHOD OF EMPLOYING SURGICAL SUTURING APPARATUS TO TIE KNOTS

BACKGROUND

1. Technical Field

This disclosure relates generally to surgical instrumentation and, more particularly, to a method of using a suturing apparatus to place knots during endoscopic or laparoscopic surgical procedures.

2. Background of the Related Art

Endoscopic or laparoscopic procedures are characterized by the use of an elongated cannula structure having a relatively small diameter with a proximal and distal end. The distal end is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure. For example, one cannula may provide a conduit for an endoscope for vision and illumination within the operative cavity while the other cannulas may provide conduits for control of specialized surgical instruments designed for performing specific procedural functions.

Many endoscopic surgical procedures call for placing stitches through tissue, a tedious procedure traditionally performed using endoscopic graspers to manipulate a needle and suture. Endoscopic suturing presents a particularly challenging task, because it must be accomplished through a port that typically averages between five and ten millimeters.

Improved instruments for facilitating endoscopic suturing are discussed in British Patent Application No. 2260704, published Apr. 28, 1993; U.S. patent application Ser. No. 08/134,145 filed Oct. 8, 1993; and U.S. patent application Ser. No. 08/319,841, filed Oct. 7, 1994. Endoscopic suturing devices such as those described in the foregoing disclosures provide a significant advantage over the traditional method of passing a needle between two endoscopic grasping instruments. However, in order to prevent the suture line from being "pulled out", the suture line must be secured at both ends, and this task poses a challenge. One solution is provided in U.S. application Ser. No. 08/134,145 in the form of suture anchor deployed from the apparatus. That, however, only secures the line of stitching at the beginning of the line. It would be advantageous to provide a method of using an endoscopic suturing instrument to form knots so that the line of stitching may be secured at any point in the stitching process using only the suture material already present in the stitches, i.e., to tie a knot in the suture to secure the suture and tissue.

SUMMARY

A number of methods are provided for tying knots in sutures using an endoscopic suturing apparatus which passes a suture needle back and forth between a pair of jaws. The apparatus is equipped with two jaws that open and close, and, when closed, can pass a surgical needle, threaded with surgical suture, back and forth between them. A more detailed description of such an instrument may be found in U.S. patent application Ser. Nos. 08/134,145 and 08/319,837, mentioned above, the disclosures of which are hereby incorporated into this application by reference.

The suturing instrument, loaded with a threaded surgical needle, is inserted into a body cavity via a surgical trocar. An endoscopic grasping device is inserted into the body cavity through a second trocar in close proximity to the suturing apparatus. The jaws of the suturing apparatus are placed around the tissue desired to be sutured (or through which a line or lines of suturing have already been placed) and one of the following methods is employed to achieve a particular knot.

To form a square knot, the operator passes the sutured needle through the tissue leaving a free portion as a tail end and, with the jaws open and the needle in one jaw, lays the suture extending from the needle over the top of the "empty" jaw (the jaw not holding the needle). The operator then grasps the tail end of the suture with the grasping device and places the jaws of the suturing device on either side of the tail end. The operator then closes the jaws and passes the needle from one jaw to the other to form a suture loop. The jaws are opened with the needle in the second jaw and the jaw containing the needle is then pulled through that loop, the jaws of the apparatus are closed and the jaws are pulled away from the knot while the tail end of the suture is held with the grasping device. The jaws are again opened and the steps outlined above are repeated in reverse order with respect to the jaws in order to create a square knot.

To form a modified fisherman's knot, the operator passes the sutured needle through the tissue leaving a free portion as a tail end and grasps the tail end of the suture with a grasping device. The jaws are opened and placed on either side of the tail end of the suture, placing the needle in front of the tail end. The jaws are closed, the needle is transferred to the opposite jaw and the jaws are opened and moved away from the tail end of the suture, thus creating a loop around the tail end. This process is repeated at least one more time, and preferably at least three more times, to create, preferably, at least four loops. The empty jaw is then inserted into the loop formed adjacent the tissue, the jaws are closed, the needle is passed to the opposite jaw, the jaws are opened and the jaws are pulled away from the loop, thereby passing the suture adjacent the tissue through the loop between the suture tail and the first suture loop. The suturing apparatus is closed and the knot is tightened to the desired tension.

The modified fisherman's knot may be further secured by creating the first half of the square knot, outlined above, around the tail end above the modified fisherman's knot, i.e., by laying the suture extending from the needle over the top of the empty jaw, placing the jaws on either side of the tail end, passing the needle from one jaw to the other to form a loop, and pulling the jaw containing the needle through that loop.

To place a securing knot, such as at the end of a line of "running" stitches, a final running stitch is created, leaving excess suture so that a loop, rather than a tightened stitch, is formed. The jaws are opened and pulled away from the tissue while a grasping device holds the loop formed. The needle is transferred to the opposite jaw and the jaws are placed on either side of the loop of suture, placing the needle in front of the loop. The needle is then transferred to the opposite jaw and the jaws are opened and moved away from the loop of suture to form a loop around the loop grasped by the grasping device. This process is repeated to form a number of such loops, preferably at least four. The securing knot may be "tied off" using the first half of a square knot as outlined above in the modified fisherman's knot. Thus, a modified fisherman's knot is formed around the loop grasped by the grasper to further secure the running stitch.

In an alternative embodiment, a square knot may be placed using the instrument. The jaws are closed around the tissue and the sutured needle is passed from one jaw to the other and drawn through the tissue, leaving a free portion as a tail end. The tail end is grasped by a grasping device. The jaws are then brought around the tail end. Using the grasping device, the tail end is wrapped once around the empty jaw, the jaws are closed and the needle is transferred to the other jaw. The jaws are opened and the jaw now containing the needle is pulled through the loop formed around that jaw, the jaws are closed and the knot is tightened to the desired tension. The second half of the alternative square knot is formed by repeating the steps outlined above in reverse.

A surgeon's knot may be formed by wrapping the free end of the suture around the empty jaw twice instead of once during the formation of the first half of the alternative square knot, outlined above.

Advantageously, similar steps are repeated in various combinations to readily form surgical knots of great importance to the surgeon.

BRIEF DESCRIPTION OF THE DRAWINGS

Preferred embodiments are described herein with reference to the drawings, in which:

FIG. 1 is a perspective view of the jaws of a surgical suturing apparatus that have drawn a piece of suture through tissue;

FIG. 2 is a perspective view of the laws of a surgical suturing apparatus with a piece of suture being laid over the empty jaw;

FIG. 3 is a perspective view of the jaws of a surgical suturing apparatus in close proximity to a tail end of suture that is being held by a grasping device;

FIG. 4 is a perspective view of the jaws of a surgical suturing apparatus in close proximity to a tail end of suture that is being held by a grasping device;

FIG. 5 is a perspective view of the jaws of a surgical suturing apparatus forming a loop of suture around a tail end of that suture which is being held by a grasping device;

FIG. 6 is a perspective view of the jaws of a surgical suturing apparatus which are closed and are tightening a loop of suture around a tail end of that suture held by a grasping device;

FIG. 7 is a perspective view of the jaws of a surgical suturing apparatus with a length of suture extending from a loop of suture around a tail end of that suture held by a grasping device;

FIG. 8 is a perspective view of the jaws of a surgical suturing apparatus as shown in FIG. 7 with a length of suture laying over the empty jaw;

FIG. 9 is a perspective view of the jaws of a surgical suturing apparatus as shown in FIG. 8 placed on either side of a tail end of suture held by a grasping device;

FIG. 10 is a perspective view of the jaws of a surgical suturing apparatus forming another loop of suture around the tail end of the suture held by a grasping device;

FIG. 11 is a perspective view of the jaws of a surgical suturing apparatus tightening a square knot made in a suture, with the tail end of the suture held by a grasping device;

FIG. 12 is a perspective view of the jaws of a surgical suturing apparatus that have drawn a piece of suture through tissue;

FIG. 13 is a perspective view of the jaws of a surgical suturing apparatus that have drawn a piece of suture through tissue with the tail end of the suture held by a grasping device;

FIG. 14 is a perspective view of the jaws of a surgical suturing apparatus forming a loop of suture around a tail end of the suture held by a grasping device;

FIG. 15 is a perspective view of the jaws of a surgical suturing apparatus forming a loop of suture around a tail end of the suture held by a grasping device;

FIG. 16 is a perspective view of the jaws of a surgical suturing apparatus forming a loop of suture around a tail end of the suture held by a grasping device;

FIG. 17 is a perspective view of the jaws of a surgical suturing apparatus forming a third loop of suture around a tail end of the suture held by a grasping device;

FIG. 18 is a perspective view of the jaws of a surgical suturing apparatus having formed four loops of suture around a tail end of the suture held by a grasping device, with the jaws being placed through the first loop adjacent tissue;

FIG. 19 is a perspective view of the jaws of a surgical suturing apparatus having formed four loops of suture around a tail end of the suture held by a grasping device, with the needle held by the jaw extending through the first loop;

FIG. 20 is a perspective view of the jaws of a surgical suturing apparatus which are drawing the suture between the tissue and the first loop in the suture;

FIG. 21 is a perspective view of the jaws of a surgical suturing apparatus which are closed, tightening a modified fisherman's knot made in the suture;

FIG. 22 is a perspective view of the jaws of a surgical suturing apparatus placing an additional loop of suture above the modified fisherman's knot made in the suture as shown in FIG. 21;

FIG. 27 is a perspective view of the jaws of a surgical suturing apparatus, having made a stitch, drawn away from tissue;

FIG. 28 is a perspective view of the jaws of a surgical suturing apparatus, having made a stitch and a loop, with the loop held by a grasping device;

FIG. 29 is a perspective view of the jaws of a surgical suturing apparatus having formed a modified fisherman's knot around the loop of suture at the end of the running stitch;

FIG. 30 is a perspective view of the jaws of a surgical suturing apparatus which are closed, after placing an additional loop of suture around the modified fisherman's knot made in the suture around the suture loop of FIG. 28;

FIG. 35 is a perspective view of the jaws of a surgical suturing apparatus of FIG. 34 with the needle and suture pulled through the loop of suture made by wrapping the suture around a jaw;

FIG. 36 is a perspective view of the jaws of a surgical suturing apparatus which are closed, tightening a knot throw made in suture;

FIG. 37 is a perspective view of the jaws of a surgical suturing apparatus of FIG. 36 which are open and placed around the tail end of suture;

FIG. 38 is a perspective view of the jaws of a surgical suturing apparatus with the tail end of the suture wrapped over the jaw of the apparatus not holding the needle;

FIG. 39 is a perspective view of the jaws of a surgical suturing apparatus of FIG. 38 with the needle passed to the jaw around which the tail end of the suture is wrapped;

FIG. 40 is a perspective view of the jaws of a surgical suturing apparatus of FIG. 39 with the needle and suture pulled through the loop of suture made by wrapping the suture around a jaw;

FIG. 41 is a perspective view of the jaws of a surgical suturing apparatus which are closed, tightening the square knot;

DESCRIPTION OF THE PREFERRED EMBODIMENTS

Figure 23:
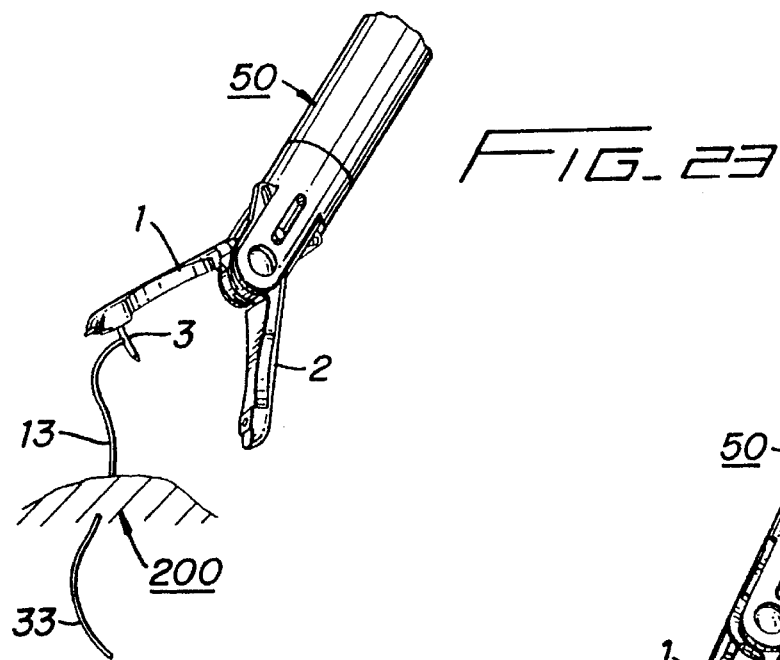
FIG. 23 is a perspective view of the jaws of a surgical suturing apparatus which are open and have drawn a piece of suture through tissue.

Each embodiment detailed below describes a method for making a knot using an endoscopic suturing device having a pair of jaws that can pass a needle with a length of suture attached back and forth between the jaws.

Referring to FIG. 1, each embodiment will be described with reference to a surgical suturing apparatus 50 having two jaws (1 and 2) which can open and close and a needle 3 which can be passed between jaws 1 and 2 when jaws 1 and 2 are closed. Referring to FIG. 2, a grasping device 100 is also employed during various stages of forming the knots. For each knot, suturing apparatus 50, loaded with a threaded surgical needle 3, is inserted into a body cavity via a surgical trocar (not shown). An endoscopic grasping device 100 is also inserted into the body cavity though a separate trocar suitably located relative to the suturing apparatus. The jaws of the suturing apparatus are placed around at least one piece of tissue 200 to be sutured (or through which a line or lines of suturing have already been placed by the suturing apparatus) and one of the following knots is made.

The Square Knot

Referring to FIG. 1, surgical suturing apparatus 50 is used to make a square knot in tissue 200. The apparatus 50 has two jaws (1 and 2) which open and close and a needle 3 which can be passed between jaws 1 and 2 when the jaws are closed. Needle 3 may start out, for example, in jaw 2. Jaws 1 and 2 are closed around tissue 200, needle 3 is transferred from jaw 2 to jaw 1, the jaws are opened and instrument 50 is drawn away from tissue 200, thus pulling needle 3 and the attached length of suture through tissue 200. These steps create the tail end of the suture 5 and the portion of suture 4 which has passed through the tissue, both extending from opposite sides of the tissue 200 as shown in FIG. 1.

Referring to FIG. 2, the length of suture 4 extending from the needle 3 is laid over the top of the "empty" jaw 2 (the jaw not holding the needle). Referring to FIG. 3, the tail end of the suture 5 is grasped with the grasping device 100 and jaws 1 and 2 of the suturing apparatus are placed on either side of tail end 5, with needle 3 in front of tail end 5 as shown in FIG. 3 and suture 4 laid across jaw 2 inside the jaws relative to tail end 5. Alternatively, depending on space availability, grasping device 100 may be used to place tail end 5 between jaws 1 and 2 rather than moving the jaws around the tail end. Reference may be made to either method throughout this description. These methods are, for all intents and purposes of knot-tying, interchangeable. Jaws 1 and 2 are then closed and, as shown in FIG. 4, needle 3 is passed from jaw 1 so that the needle now resides in jaw 2 with suture 4 extending from needle 3 wrapped around tail end 5. Referring to FIG. 5, jaw 2 is then pulled through the first knot throw suture loop 6 formed by portion 4 wrapped around tail end 5.

Referring to FIG. 6, the jaws of the apparatus 1 and 2 preferably are closed and the length of suture 31 attached to needle 3 is pulled while the tail end of the suture 5 is held with the grasping device to tighten the first throw of the knot to the desired tension. Closing the jaws while tensioning the suture is preferred to balance the force on the jaws and needle. It is contemplated, however, that the suture could be tensioned with the jaws open.

Referring to FIG. 7, jaws 1 and 2 are again opened with needle 3 in jaw 2 and, as shown in FIG. 8, the suture 31 extending from the needle 3 to the first knot throw is laid over the top of the "empty" jaw 1. Referring to FIG. 9, the tail end of the suture 5 is placed, using grasping device 100, between jaws 1 and 2. Jaws 1 and 2 are closed and, as shown in FIG. 10, needle 3 is passed from jaw 2 to jaw 1 and jaw 1 is pulled through the loop of suture formed by portion 31 to create a second knot throw loop 7. Referring to FIG. 11, the jaws of the apparatus 1 and 2 preferably are closed and the length of suture 31 attached to the needle 3 is pulled while continuing to hold the tail end of the suture 5 with the grasping device 100, thus forming a square knot.

The Modified Fisherman's Knot

Referring to FIG. 12, a surgical suturing apparatus 50 is used to make a modified fisherman's knot in tissue 200. The apparatus 50 has two jaws (1 and 2) which can be opened and closed and a needle 3 which can be passed between jaws 1 and 2 when the jaws are closed. Needle 3 may start out, for example, in jaw 2. Jaws 1 and 2 are closed around tissue 200, needle 3 is transferred from jaw 2 to jaw 1, the jaws are opened and instrument 50 is drawn away from tissue 200, thus pulling needle 3 and the attached length of suture 35 through tissue 200. These steps create the tail end of the suture 8 and the portion of suture 35, both extending from opposite sides of the tissue 200 as shown in FIG. 12.

Referring to FIG. 13, the tail end of the suture 8 is held using a grasping device 100 and the needle 3 is transferred from jaw 1 to jaw 2. As shown in FIG. 14, jaws 1 and 2 are moved so that tail end 8 is between them and needle 3 is front of tail end 8. Jaws 1 and 2 are then closed and needle 3 is transferred from jaw 2 to jaw 1, resulting in the arrangement portrayed in FIG. 15. As shown in FIG. 16, open jaws 1 and 2 are moved away from tail end of the suture 8, creating a loop 9 around tail end 8. This process is repeated a number of times to create several more loops around tail end 8, i.e., jaws 1 and 2 are closed, needle 3 is transferred to the opposite jaw, jaws 1 and 2 are opened and moved so that tail end 8 is between them and needle 3 is front of tail end 8. Jaws 1 and 2 are then closed and needle 3 is transferred back to the other jaw, jaws 1 and 2 are then opened and moved away from the tail end of the suture 8, creating another loop around tail end 8 and so on until the desired number of loops, such as 9, 10, 11 and 12 have been created as shown in FIG. 17. Preferably, these steps are repeated at least four times to create at least three loops around tail end 8.

As shown in FIG. 18, needle 3 is transferred to jaw 2 and empty jaw 1 is inserted into the loop formed adjacent the tissue by suture portion 7. Jaws 1 and 2 are closed, needle 3 is passed from jaw 2 to jaw 1, and jaws 1 and 2 are opened as shown in FIG. 19. Jaw 1 containing needle 3 is pulled through the loop formed by portion 35 as shown in FIG. 20. Jaws 1 and 2 preferably are then closed and the knot is tightened to the desired tension as shown in FIG. 21, always holding tail end 8 in grasping device 100. The knot may be moved into close proximity adjacent to tissue 200 by applying tension to tail end 8 and urging the knot toward the tissue with the suturing apparatus or another device.

As shown in FIG. 22, the modified fisherman's knot may be further secured by performing the first half of the square knot outlined above in FIGS. 1–6, i.e., by opening the jaws 1 and 2 with the needle in jaw 1 and laying the suture extending from the needle 3 over the top of the "empty" jaw 2. As described above, the free end of the suture 8 (still grasped with the grasping device 100) is placed between the jaws of the suturing apparatus 1 and 2. Jaws 1 and 2 are then closed and needle 3 is passed from jaw 1 to jaw 2. Jaw 2 is then pulled through the loop of suture formed around tail end 8 by these last steps to create knot throw loop 32 as depicted in FIG. 22 and is tightened to the desired tension.

The Securing Knot

A securing knot is often desirable at the end of a line of stitches to prevent the line of stitches from pulling out of the tissue. As shown in FIGS. 23–27, a running stitch is placed using the endoscopic suturing device by passing the needle back and forth between jaws 1 and 2 while penetrating tissue 200 with needle 3. More specifically, needle 3 may start out, for example, in jaw 2. Jaws 1 and 2 are closed around tissue 200, needle 3 penetrates tissue 200 and is transferred from jaw 2 to jaw 1, the jaws are opened and instrument 50 is drawn away from tissue 200, thus pulling needle 3 and the attached length of suture through tissue 200. These steps create the tail end of the suture 33 and a portion of suture 13, both extending from opposite sides of the tissue 200 as shown in FIG. 23.

Figure 24:
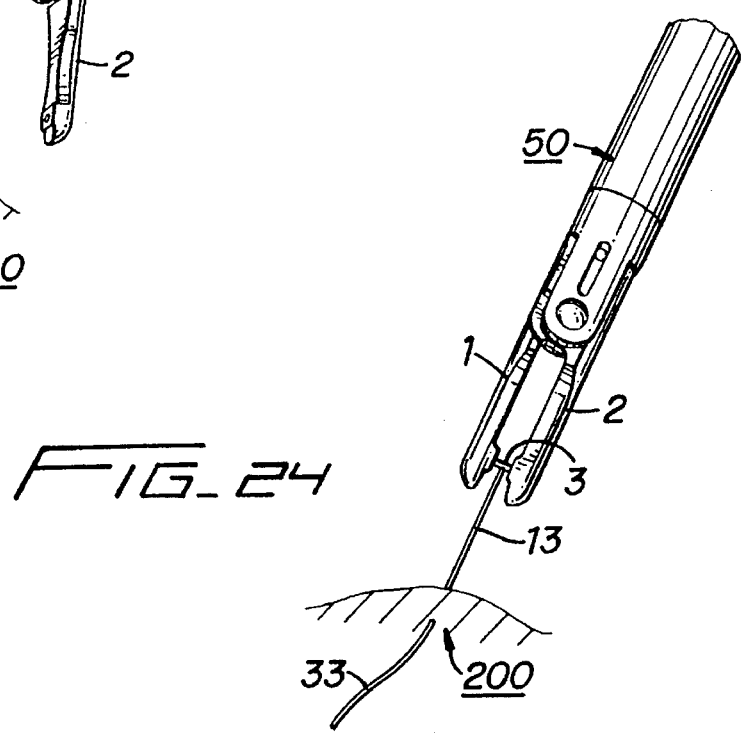
FIG. 24 is a perspective view of the jaws of a surgical suturing apparatus which are closed to draw a piece of suture through tissue.
Figure 25:
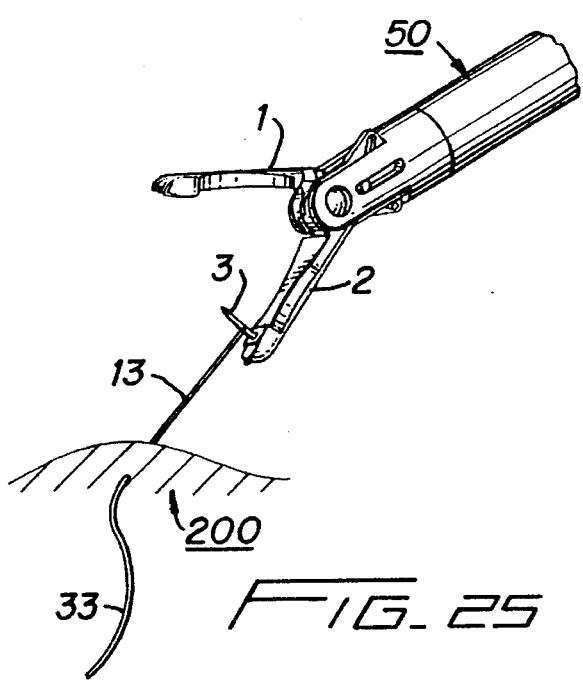
FIG. 25 is a perspective view of the jaws of a surgical suturing apparatus which are open after a length of suture has been drawn through tissue and the needle passed to the opposite jaw of FIG. 23.
Figure 26:
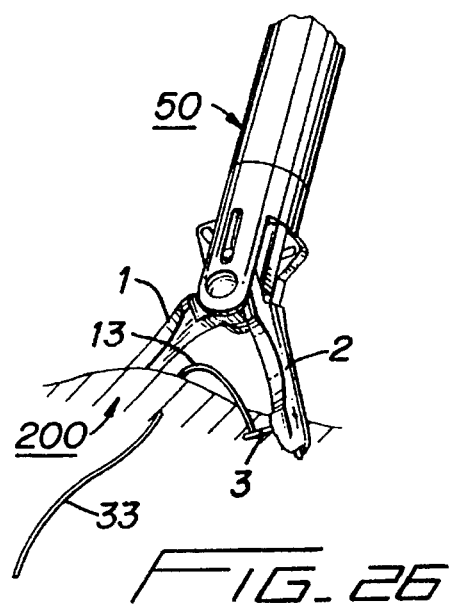
FIG. 26 is a perspective view of the jaws of a surgical suturing apparatus piercing tissue with the empty jaw placed inside a suture loop in tissue.

The jaws are closed as shown in FIG. 24, and the needle 3 is passed from jaw 1 to jaw 2. The jaws are then opened again, resulting in the configuration of FIG. 25. The jaws are then brought toward tissue 200 so that a portion of tissue 200 adjacent tail end 33 resides between the jaws, and the jaws are closed as shown in FIG. 26, thus piercing a second location on tissue 200. The needle 3 is transferred from jaw 2 to jaw 1 and the jaws are opened and pulled away from the sutured tissue as illustrated in FIG. 27, to apply the desired tension to stitch 13. One stitch 13 has now been placed in tissue 200. This process is repeated as many times as desired to make a line of running stitches of the appropriate length.

When making the final stitch in the line of running stitches, additional length of suture is left so that the last "stitch" is actually a loop as shown by loop 14 in FIG. 28. As shown in FIG. 28, loop 14 is held by grasping device 100.

The open jaws 1 and 2 are moved toward loop 14 and placed so that loop 14 resides between the open jaws and needle 3 is front of loop 14, as outlined above for the modified fisherman's knot and shown in FIG. 14. Loops 17, 18, 19 and 20 are created around loop 14 by the same motions that created loops 9, 10, 11 and 12 in FIGS. 14–18, i.e., the jaws repeatedly are placed on either side of loop 14, the jaws are closed, the needle 3 is transferred from one jaw to the other, the jaws are opened, and the jaws are drawn away from the loop 14 as outlined above for the modified fisherman's knot shown in FIGS. 14–16, until the desired number of loops is created. In FIG. 29, four throw loops are formed around loop 14. Also as illustrated in FIG. 29, the needle has been passed to an empty jaw, placed between the tissue and the first loop 17, the jaws have been opened, and the needle and suture have been drawn through the space between the tissue and first loop 17 in a manner similar to that portrayed in FIGS. 19 and 20. The modified fisherman's knot may then be tightened and drawn to the tissue.

As with the modified fisherman's knot, a further securing knot may be placed by performing the first half of the square knot outlined above in FIGS. 1–6, i.e., by opening the jaws 1 and 2 and laying the suture extending from the needle 3 over the top of the "empty" jaw, for example, jaw 2. As described above, loop 14 continues to be grasped with the grasping device 100 and is placed between the jaws of the suturing apparatus 1 and 2. Jaws 1 and 2 are then closed and needle 3 is passed from jaw 1 to jaw 2 to wrap suture 21 around loop 14. Jaw 2 is then pulled through the loop of suture formed by these last steps to create a knot throw loop 22 as depicted in FIG. 30. This final loop is then tightened to the desired tension.

The Alternative Square Knot

Figure 31:
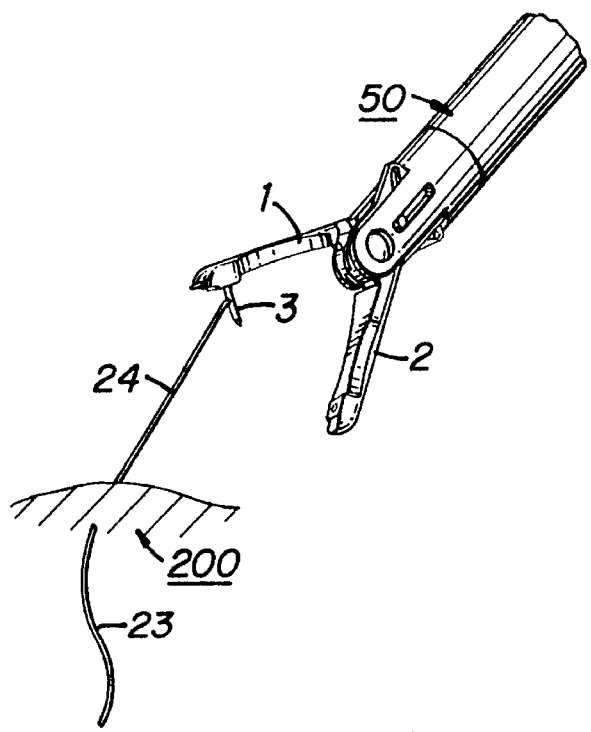
FIG. 31 is a perspective view of the jaws of a surgical suturing apparatus that has drawn a length of suture through tissue.

Referring initially to FIG. 31, surgical suturing apparatus 50 is used to make an alternative square knot in tissue 200. Jaws 1 and 2 are closed around tissue 200, needle 3 penetrates tissue 200 and is transferred from jaw 2 to jaw 1, the jaws are opened and instrument 50 is drawn away from tissue 200, thus pulling needle 3 and the attached length of suture 24 through tissue 200. These steps create the tail end of the suture 23 and the portion of suture 24 attached to needle 3, both extending from opposite sides of the tissue 200 as shown in FIG. 31.

Figure 32:
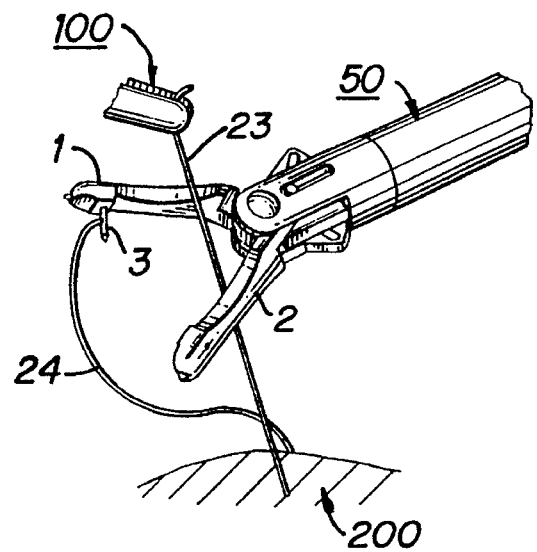
FIG. 32 is a perspective view of the jaws of a surgical suturing apparatus with the jaws open around a tail end of the suture held by a grasping device.
Figure 33:
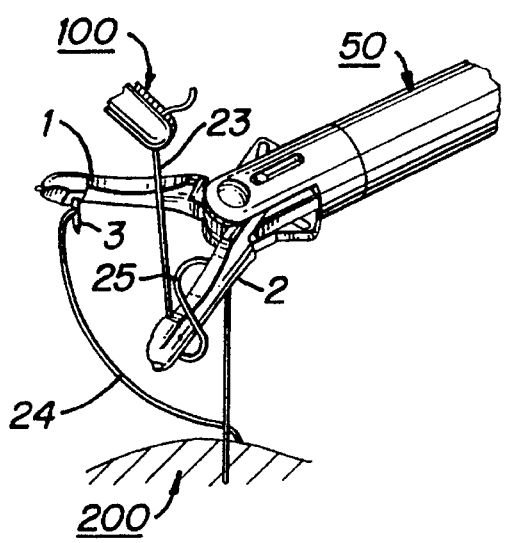
FIG. 33 is a perspective view of the jaws of a surgical suturing apparatus with the tail end of suture wrapped around one of the jaws and the suture tail end held by a grasping device.
Figure 34:
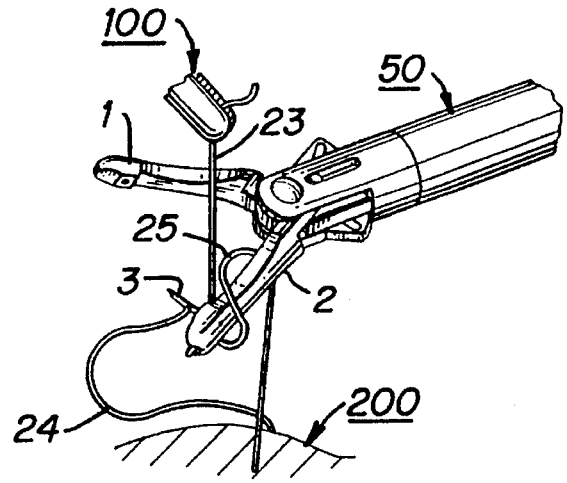
FIG. 34 is a perspective view of the jaws of a surgical suturing apparatus with the needle passed to the jaw around which the tail end of suture is wrapped.

Tail end 23 is held by a grasping device 100 and the jaws 1 and 2 are placed on either side of tail end 23 as shown in FIG. 32. Using the grasping device 100, tail end 23 is wrapped once around jaw 2 ("the empty jaw") as shown in FIG. 33 to form loop 25. The jaws are closed and the needle is transferred from jaw 1 to jaw 2, and the jaws are opened as shown in FIG. 34. As shown in FIG. 35, the jaws are pulled away from tail end 23, pulling suture portion 24 through loop 25. The jaws 1 and 2 preferably are closed and this portion of the knot is pulled to the desired tension as shown in FIG. 36.

To form the second half of the alternative square knot, the jaws 1 and 2 are opened with needle 3 in jaw 2. Jaws 1 and 2 are placed on either side of tail end 23 as shown in FIG. 37 and tail end 23 is wrapped around jaw 1 using grasping device 100 as shown in FIG. 38, creating loop 26. Jaws 1 and 2 are then closed and needle 3 is transferred from jaw 2 to jaw 1. Jaws 1 and 2 are opened as shown in FIG. 39 and, as shown in FIG. 40, jaw 1 holding needle 3 is drawn through loop 26. As shown in FIG. 41, jaws 1 and 2 preferably are closed and the knot is tightened to the desired tension.

The Surgeon's Knot

Figure 42:
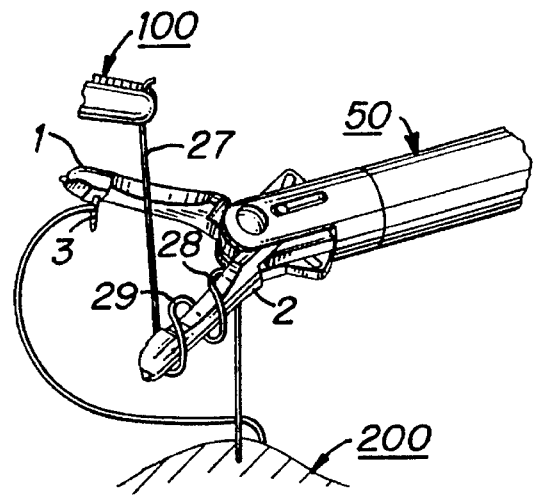
FIG. 42 is a perspective view of the jaws of a surgical suturing apparatus with two loops made of the tail end of the suture around one of the jaws of the apparatus.
Figure 43:
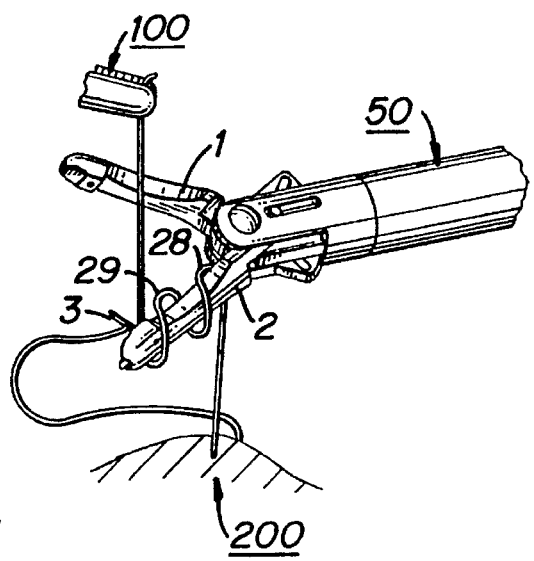
FIG. 43 is a perspective view of the jaws of the surgical suturing apparatus of FIG. 42 with the needle passed to the jaw wrapped with the suture tail end.
Figure 44:
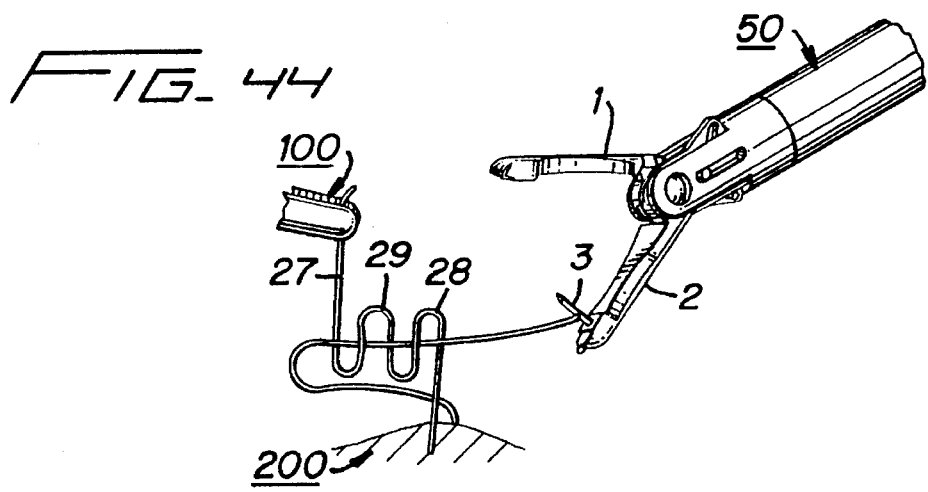
FIG. 44 is a perspective view of the surgical suturing apparatus of FIG. 43 with the needle and suture drawn through the loops formed by wrapping the tail end of the suture around a jaw of the apparatus.

Alternatively, a surgeon's knot may be formed by following steps similar to those outlined above for the alternative square knot. However, when wrapping the tail end of the suture around the empty jaw during formation of the first half of the knot,(compare FIGS. 33 and 34), the tail end of the suture is wrapped around the empty jaw twice instead of once. The double-wrapping technique is shown in FIG. 42 which depicts loops 29 and 28 being made around jaw 2. Then, similar to the alternative square knot, needle 3 is transferred from jaw 1 to jaw 2, as shown in FIG. 43, and, as shown in FIG. 44, needle 3 and its corresponding length of suture are drawn through loops 28 and 29. This forms the first half of the surgeon's knot. The second half of the surgeon's knot is formed by performing the steps outlined above for the second half of the alternative square knot, as shown in FIGS. 37–41, i.e., the tail end of the suture is only wrapped once around the empty jaw, as shown in FIGS. 38 and 39. The surgeon's knot is then tightened to the desired tension. A double surgeon's knot may be accomplished by placing two loops of suture around the empty jaw, as described above, during formation of both halves of the knot.

It will be understood that various modifications may be made to the embodiments disclosed herein. For example, two lengths of suture from the two lines of stitches could be tied together using the apparatus described herein. By way of further example, the preferred embodiments have all been illustrated in the attached drawings with reference to an apparatus having two movable jaws with a double ended needle or surgical incision member with the suture attached to the middle of the needle. The disclosed method is equally applicable to other endoscopic suturing devices such as, for example, devices with only one movable jaw and/or having a single pointed needle with the suture attached at an end of the needle, such as the device disclosed in British Patent Application No. 2260704. It is also contemplated that any of these knots may be formed around tissue or other anatomical structure rather than passing the needle through the tissue. By way of example only, a knot may be formed around an artery or duct to tie off or occlude the artery or duct. Therefore, the above description should not be construed as limiting, but merely as exemplifications of the preferred embodiments. Those skilled in the art will envision other modifications within the scope and spirit of the claims appended hereto.

We claim:

1. A method for forming a knot during endoscopic surgery using a surgical apparatus including the steps of:

providing a surgical instrument having first and second jaws which open and close and a surgical needle with length of suture attached, the needle operatively connected to the jaws so that it may be passed between them;

passing the needle and a portion of the suture through a piece of tissue to create a first suture portion attached to the needle on one side of the tissue and a second suture portion on the other side of the tissue;

creating a first loop of suture around the second portion of suture using the first portion of suture by passing the needle between the jaws.

2. The method of claim 1, further including the step of creating a second loop of suture around the second portion of suture using the first portion of suture by passing the needle between the jaws.

3. The method of claim 2, further including the steps of:

creating a third loop of suture around the second portion of suture using the first portion of suture;

creating a fourth loop of suture around the second portion of suture using the first portion of suture; and pulling the first portion of suture between the first loop of suture and the tissue.

4. The method of claim 3, further including the steps of:

creating a fifth loop of suture around the second portion of suture using the first portion of suture; and passing the first portion of suture through the fifth loop.

5. The method of claim 1, further including the step of grasping the second portion of suture with a grasping device.

6. The method of claim 1, further including the step of forming a plurality of loops of suture around the second portion of suture by sequentially passing the needle back and forth from one jaw to the other with the second suture portion between the jaws.

7. The method of claim 6, further including the steps of:

inserting a jaw of the instrument between the tissue and the first suture loop with the second suture portion between the jaws;

passing the needle to the jaw so inserted; and drawing the needle and first suture portion through the space between the tissue and the first loop to form a knot.

8. A method for forming a knot using a surgical apparatus including the steps of:

providing a surgical instrument having a first jaw and a second jaw which open and close, and a surgical needle with length of suture attached, the needle operatively connected to the jaws so that the needle may be passed between them;

passing the needle and suture through a piece of tissue to create a first portion of suture attached to the needle on one side of the tissue and a second portion of suture on the other side of the tissue;

passing the first portion of suture through a piece of tissue to create a first loop affixed in the tissue; and creating a second loop of suture around the first loop of suture using the first portion of suture by passing the needle from one jaw to the other.

9. The method of claim 8, further including the steps of:

creating a third loop of suture around the first loop of suture using the first portion of suture;

creating a fourth loop of suture around the first loop of suture using the first portion of suture; and pulling the first portion of suture between the second loop of suture and the tissue.

10. The method of claim 8, further including the steps of:

creating a plurality of loops of suture around the first loop of suture using the first portion of suture by passing the needle from one jaw to the other; and passing the first portion of suture between the second loop of suture and the tissue.

11. The method of claim 9, further including the step of creating a fifth loop of suture around the first loop of suture using the second portion of suture.

12. The method of claim 10, further including the step of grasping the first loop of suture with a grasping device while the plurality of loops are formed.

13. A method for forming a knot using a surgical apparatus including the steps of:

providing a surgical instrument having a first jaw and a second jaw which open and close and a surgical needle with length of suture attached, the needle operatively connected to the jaws so that it may be passed between them;

passing the needle and a portion of the suture through a piece of tissue to create a first suture portion attached to the needle on one side of the tissue and a second suture portion on the other side of suture on either side of the tissue;

creating a first loop of suture around the first jaw not holding the needle using the second portion of suture;

passing the needle to the first jaw; and pulling the first portion of suture through the first loop of suture.

14. The method of claim 13 further including the steps of:

creating a second loop of suture around the second jaw not holding the needle using the second portion of suture;

passing the needle to the other jaw; and pulling the first portion of suture through the second loop of suture to form a square knot.

15. A method for forming a knot using a surgical apparatus including the steps of:

providing a surgical instrument having a first jaw and a second jaw which open and close, and a surgical needle with length of suture attached, the needle being operatively connected to the jaws so that it may be passed between them;

passing the needle and a portion of the suture through a piece of tissue to create a first portion of suture attached to the needle on one side of the tissue, and a second portion of suture on the other side of the tissue;

creating at least two loops of suture around the first jaw not holding the needle using the second portion of suture;

passing the needle to the first jaw; and pulling the first portion of suture through the loops of suture formed around the first jaw.

16. The method of claim 15 further including the steps of:

creating at least one loop of suture around the second jaw not holding the needle using the second portion of suture;

passing the needle to the second jaw; and pulling the first portion of suture through at least one loop of suture formed around the second jaw.

\* \* \* \* \*